United States Patent [19]

Kapka et al.

[11] Patent Number: 5,635,398
[45] Date of Patent: Jun. 3, 1997

[54] HYBRIDIZATION VESSEL ROTATOR

[75] Inventors: Anthony S. Kapka, Philadelphia, Pa.; Richard Manzari, Mount Holly, N.J.; John A. Westenberger, Hatboro, Pa.

[73] Assignee: Boekel Industries, Inc., Feasterville, Pa.

[21] Appl. No.: 529,855

[22] Filed: Sep. 18, 1995

[51] Int. Cl.$^6$ ..................................................... C12M 3/00
[52] U.S. Cl. ........................... 435/286.7; 435/298.2; 435/809; 366/197; 366/198; 366/200; 366/220
[58] Field of Search ................................. 366/138, 197, 366/198, 200, 220; 435/286.7, 298.2, 809

[56] References Cited

U.S. PATENT DOCUMENTS 5,360,741  11/1994  Hunnell ................................. 435/290
5,380,662  1/1995  Robbins et al. ...................... 435/312

OTHER PUBLICATIONS

"Mini–Hybridization Oven" Hoefer Scientific Instruments, 1994.
"The Stovall Hybridization Oven" Stovall Life Science, Inc.
"VWRbrand Hybridization Oven" VWR Scientific.
"Instruments for Biotechnology" Stuart Scientific.
"Hybridization Ovens" Denville Scientific.
"The Biometra Family of Hybridization Ovens" Biometra.
"BELLCO AutoBlot Micro Hybridization Oven" BELLCO Glass, Inc.
"High Performance Hybridization Oven" Sheldon International Ltd.
"Robbins Hybridization Incubators" Robbins Scientific.
"The Hybaid Mini Hybridization Ovens" National Labnet Co 1993.
"Advanced, Space–Saving Personal Hybridization Oven with Low Introductory Price" *Strategies in Molecular Biology* vol. 8.
"Uniform Temperature Hybridizations" Savant Instruments, Inc.
"Mini–Hybridization Incubator" Lab–Line Instruments, Inc.
"Micro Incubator, Micro Price." Robbins Scientific Corporation.
"Shake and Incubate with the ROSI 1000 Shaking Incubator" Curtin Matheson Scientific, Inc.

*Primary Examiner*—David A. Redding
*Attorney, Agent, or Firm*—William H. Eilberg

[57] ABSTRACT

A hybridization vessel rotator can be used, without modification, in either a liquid bath or a conventional oven. The rotator includes a frame which supports a spindle to which hybridization vessels are attached. A motor turns the spindle to rotate the vessels. The motor is affixed to the frame at a position opposite to the bottom surface of the frame. The rotator can thus be inserted into a liquid bath, while the motor remains outside of the bath. If an oven is used, the entire rotator can be placed inside the oven. The vessel rotator is independent of the external source of heating or cooling. The vessel rotator also does not require that the bath or oven be specifically designed for use with the rotator.

17 Claims, 5 Drawing Sheets

FIG. 1

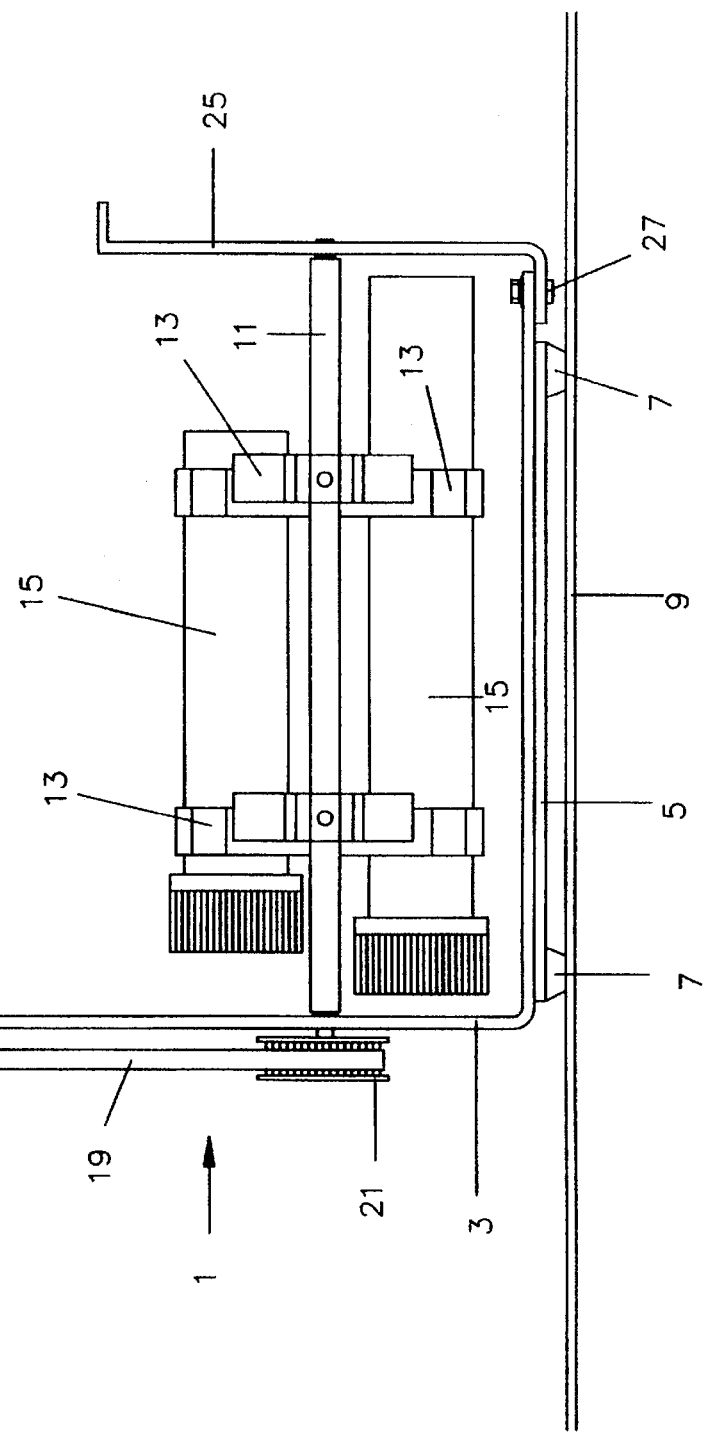

5,635,398

HYBRIDIZATION VESSEL ROTATOR

BACKGROUND OF THE INVENTION

The present invention relates to devices for promoting hybridization reactions used in genetic research or biotechnology. In particular, the present invention makes it possible to use the same vessel rotator, regardless of whether the hybridization reactions are to be conducted in dry heat, in a liquid bath, or in another temperature-controlled environment.

In DNA and RNA research, current laboratory practice requires the use of expensive dedicated dry heat incubators for use in hybridizing nitro-cellulose membranes in special glass or plastic hybridization vessels. Such incubators provide heat while slowly rotating the vessels, over a period which may be about twelve hours. Alternatively, one can use a liquid bath to promote the hybridization reaction, wherein the nitro-cellulose membranes are held in plastic bags immersed in the bath. The bath is typically agitated by vibrators, or by shaking the entire bath, or by other means, to impart the necessary motion to the bags. The latter process is older and considered less preferable than the use of dry heat incubators, but it is also much less expensive, and can be practiced, at least in theory, almost anywhere a sink or tub is found.

The prior art contains many examples of hybridization ovens which provide support and rotational movement for the vessels containing the reactants, while applying dry heat to promote the hybridization reaction. Such ovens are particularly designed for use with dry heat, insofar as the support structures which rotate the vessels form part of the ovens. Thus, such devices are inherently incompatible with the use of a liquid bath.

The present invention provides a hybridization vessel rotator device which can be used regardless of whether it is to be placed in a temperature-controlled chamber or in a temperature-controlled liquid bath. The user need not make changes in the rotator device itself.

SUMMARY OF THE INVENTION

The present invention is a hybridization vessel rotator which can be inserted in a conventional oven or immersed in a liquid bath. The rotator includes a frame which supports a spindle to which one or more hybridization vessels are connected. Rotation of the spindle thus rotates the vessels. The frame includes a base portion which preferably has feet for supporting the frame on a surface, and a pair of upright portions, preferably perpendicular to the base portion. A motor is affixed to one of the upright portions of the frame, at a position opposite to the base portion. A drive belt connects the motor to the spindle. The motor is located a sufficient distance away from the base portion and the spindle such that the device can be immersed in a liquid bath without also immersing the motor. The motor is also preferably laterally offset relative to the base portion, so that when the base portion is immersed in the bath, the motor is not directly above the bath. However, the motor is still rigidly attached to the frame, and the entire device can be inserted into a conventional oven, if dry heat is desired.

The present invention also includes the method of using the hybridization vessel rotator described above. One first determines whether the hybridization reaction is to be conducted in dry heat or in a heated liquid bath. If dry heat is selected, one inserts the entire device, described above, into an oven. One actuates the motor, to rotate the hybridization vessels, and actuates the oven to provide the heat. If a liquid bath is selected, one immerses the vessel rotator into the bath, while keeping the motor outside the bath. The base portion permits the frame to rest securely on the bottom of the bath.

The present invention therefore has the primary object of providing a hybridization vessel rotator which can be used in either an oven or a liquid bath.

The invention has the further object of reducing the cost of performing hybridization reactions, by enabling the operator to use existing incubators or liquid baths as the heat source for the hybridization process.

The invention has the further object of increasing the flexibility of the equipment available to the laboratory technician, by allowing the same equipment to be used with both dry heat ovens and warm liquid baths.

The invention has the further object of providing a hybridization vessel rotator which does not require a specially constructed liquid bath or oven, but which can be used with virtually any bath or oven.

The invention has the further object of making it feasible to switch easily between hybridization in a dry heat oven and hybridization in a warm liquid bath.

The reader skilled in the art will recognize other objects and advantages of the invention, from a reading of the following brief description of the drawings, the detailed description of the invention, and the appended claims.

BRIEF DESCRIPTION OF THE DRAWINGS

FIG. 5 provides an elevational view, similar to that of FIG. 1, showing an alternative embodiment wherein the motor is disposed directly above the rotating vessels.

DETAILED DESCRIPTION OF THE INVENTION

Figure 1:
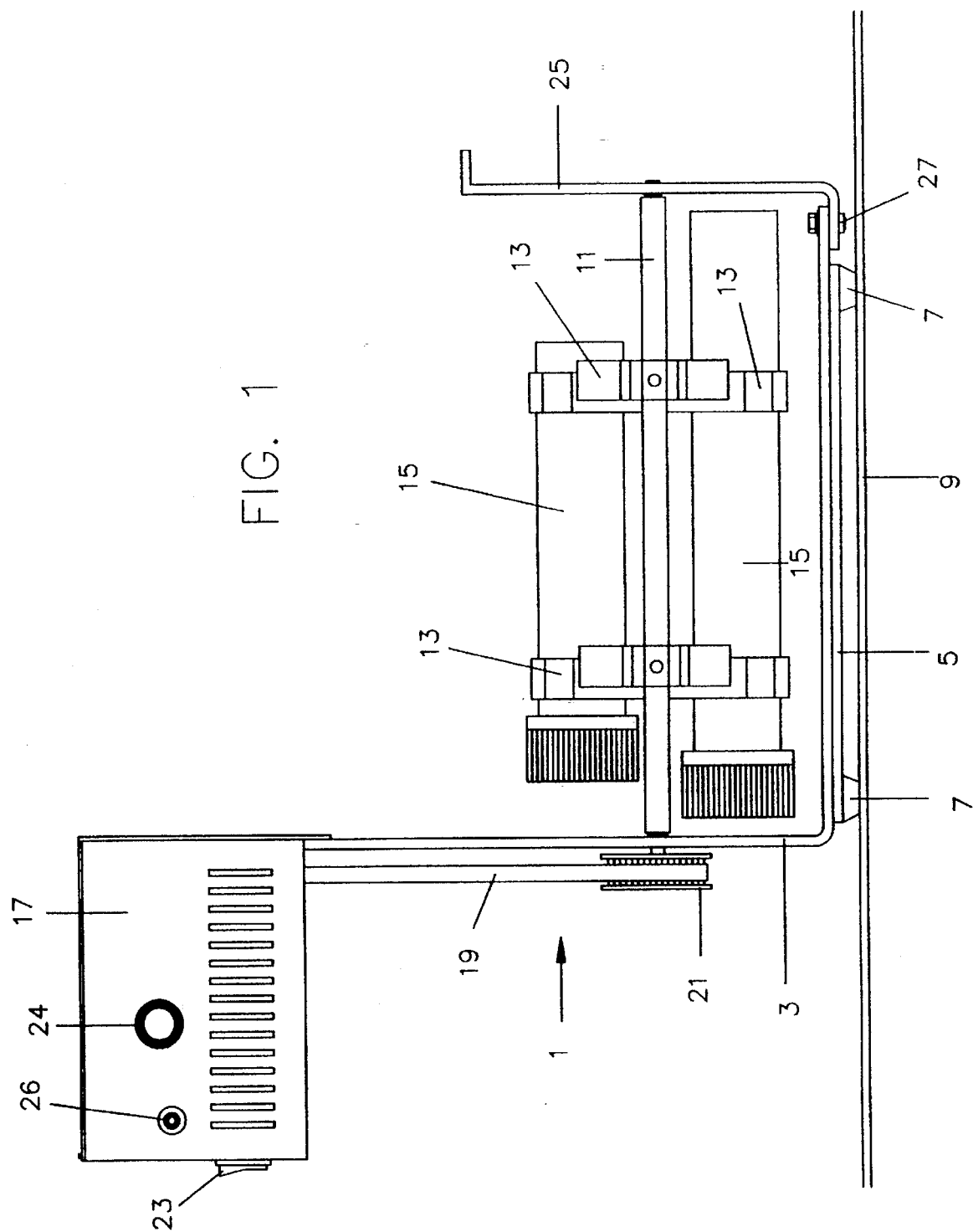
FIG. 1 provides an elevational view of the hybridization vessel rotator according to the present invention.

FIG. 1 shows the hybridization vessel rotator device 1 of the present invention. The device includes frame 3 defined by two upright portions and base portion 5. The base portion preferably includes feet 7 to enable the base portion to rest, in a stable manner, on surface 9. Frame 3 supports spindle 11 to which there are attached a plurality of spring clips 13. The spring clips comprise means for holding hybridization vessels 15. The vessels 15 can therefore be easily inserted and removed from the device. When the spindle rotates, the vessels similarly rotate.

Motor compartment 17 is affixed to one end of the frame, and is connected to spindle 11 through belt 19 and pulley 21. The motor compartment, which houses a motor and related components, is laterally offset relative to the base portion 5, and is attached to the frame at a position opposite to that of the base portion. As used herein, the term "laterally offset" means that the motor compartment is not directly above the base portion, as shown in FIG. 1.

The motor is turned on or off by switch 23. Switch 23 can therefore be used to position the spindle so that a particular vessel can be more easily attached or removed. The speed of the motor may be varied by control 24. The motor may be connected to an external power source through jack 26.

The hybridization vessel rotator can accommodate vessels which differ in size, on the same spindle, as shown for example in FIG. 1. Also, the end plate 25, which comprises one of the upright portions of the frame, is preferably attached to the frame in a removable manner, such as with bolt means 27, so that the device can be easily modified to accommodate longer spindles and hence longer vessels. The spindle itself can be easily removed from the frame, and each type of spindle may be capable of holding several hybridization vessels and/or several types of such vessels.

Figure 2:
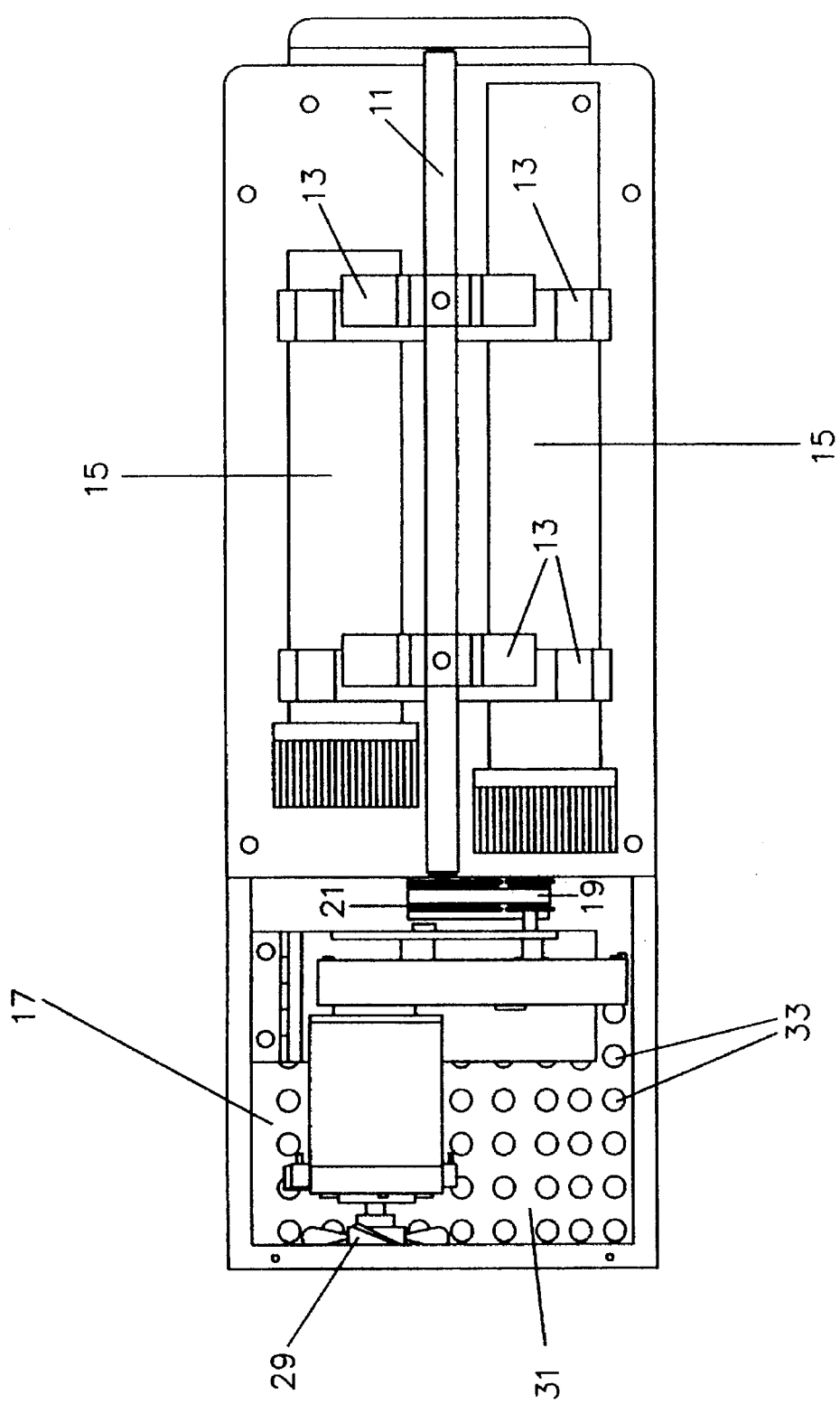
FIG. 2 provides a plan view of the hybridization vessel rotator made according to the present invention.

FIG. 2 provides a plan view showing more details of the motor compartment. As shown in FIG. 2, in addition to driving belt 19, the motor drives fan 29. The bottom portion 31 of the motor compartment has a plurality of holes 33. The fan not only cools the motor, and other electrical components in the motor compartment, but also creates a positive air flow through the holes, which tends to prevent the accumulation of condensation in the motor compartment. That is, the fan blows air across the motor, and also creates a positive air pressure downward through the holes. This feature is especially important when the device is used with a liquid bath, in which case the motor may receive some of the moisture evaporating from the bath.

Figure 3:
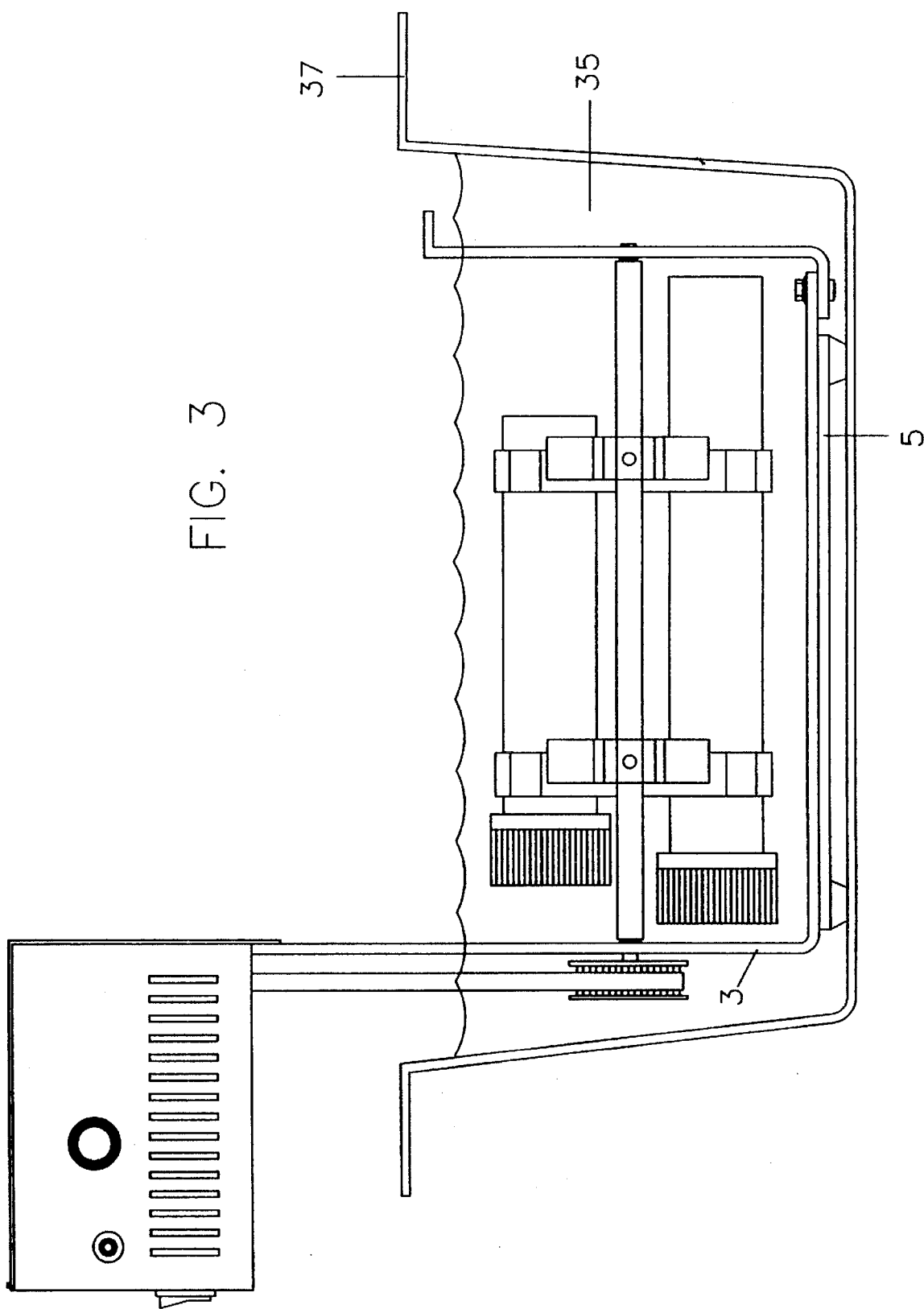
FIG. 3 provides an elevational view of the hybridization vessel rotator of the present invention, the rotator being shown immersed in a liquid bath.
Figure 4:
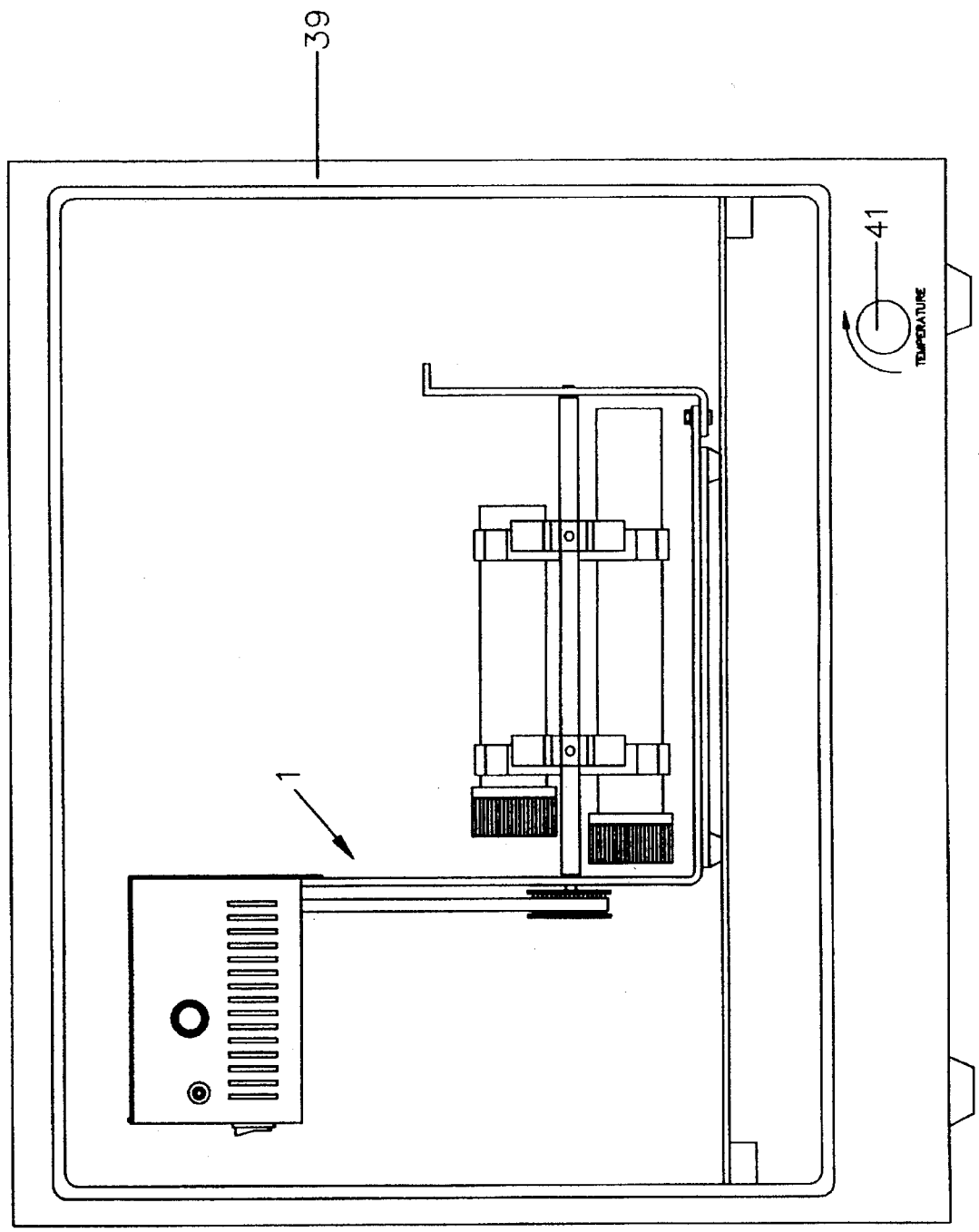
FIG. 4 provides an elevational view of the hybridization vessel rotator of the present invention, the entire device being enclosed within an oven.

FIGS. 3 and 4 show the hybridization vessel rotator used in two different modes. In FIG. 3, the device is used with a liquid bath 35 which is held within container 37. The size and weight of the base portion and frame 3 are such that the device is balanced and stable in the position illustrated, notwithstanding the laterally offset location of the motor. Moreover, the base portion comprises ballast which prevents the device from floating when in a liquid bath. As shown in FIG. 3, the motor is always held completely outside the bath, and as far from the bath as practicable, while maintaining the connection with the frame. By holding the motor in the laterally offset position such that the motor is not directly above the bath, as shown in FIG. 3, one reduces the amount of moisture that is likely to reach the motor.

In FIG. 4, the rotator device is used with a conventional oven 39. The entire device is simply placed in the oven, and the temperature is set by controller 41. It is an important feature of the present invention that the structural elements of the rotator device 1 are entirely independent of those of the oven 39. Thus, the oven need not be specifically built for use in promoting hybridization reactions. On the contrary, since the rotator device is independent, it can be placed in virtually any oven, as long as the oven is sufficiently large to accommodate it. A power cord for the device (not shown) can be routed through a flexible rubber seal which is generally provided around the edges of the doors of conventional ovens. Thus, the power cord will not prevent the oven door from being closed properly.

The invention is not limited to use with reactions which are promoted by heat. The same device can be used in applications requiring rotation of a vessel in a cooled liquid bath, or in the cool environment of a refrigerator.

For purposes of safety, the motor preferably operates at a low voltage and low current level. Therefore, in the relatively unlikely event that the motor becomes accidentally immersed in a liquid bath, there is little danger of severe electric shock.

While the hybridization vessel rotator device of the present invention is not limited to use of particular materials, it is preferred that the components be made of materials that resist corrosion and which can withstand heat.

In using the device of the present invention, one simply attaches one or more hybridization vessels to the spindle, using the clamps shown. Then, if dry heat is to be used, one places the entire device in an oven, connects the power cord, and actuates the motor while turning on the oven. If a liquid bath is to be used, one immerses the lower portion of the device (i.e. the portion which excludes the motor compartment) into the bath, so that the base portion rests securely on the bottom of the bath. The motor is then actuated, and one can also actuate a vibrator or other agitator for the bath, if desirable. The operation of the rotator device itself is therefore truly independent of the source of heat (or cold).

FIG. 5 shows an alternative embodiment wherein the motor compartment 17 is not laterally offset, but instead is located directly over at least a part of the base portion. The embodiment of FIG. 5 has the advantage that it is generally more compact, and may therefore fit more easily into an oven than the embodiment of FIG. 1. The embodiment of FIG. 5 can still be used with a liquid bath, because the motor compartment is still held above the base portion, and does not become immersed in the bath. However, the embodiment of FIG. 5 has the disadvantage that evaporated liquid from the bath is more likely to enter the motor compartment. The embodiment of FIG. 5 is otherwise similar to that of FIG. 1.

While the invention has been described with respect to a particular preferred embodiment, the invention may be modified in various ways. For example, the number and shape of the clips and vessels can change, and the components inside the motor compartment can be arranged in different ways. The invention can be practiced with frames having differing shapes which fulfill the needs of specific applications. As noted above, the oven may be replaced with a refrigerator or other temperature-controlled chamber. Similarly, the liquid bath may be temperature-controlled so as to be cool or warm. These and other modifications should be considered within the spirit and scope of the following claims.

What is claimed is:

1. A hybridization vessel rotator including means for holding a plurality of hybridization vessels and means for rotating said vessels, the improvement wherein:

a) the means for holding hybridization vessels is supported by a frame which includes a base portion, and b) the rotating means comprises a motor which is affixed to the frame, at a position opposite to the base portion, wherein the frame includes an end plate which is removably attached to the base portion.

2. The improvement of claim 1, wherein the motor is laterally offset relative to the base portion.

3. The improvement of claim 1, wherein at least a portion of the motor is disposed directly above the base portion.

4. The improvement of claim 1, wherein the motor is disposed in a housing, the improvement further comprising blower means for creating a positive air flow across the motor and in the housing, thereby reducing condensation.

5. In combination, a hybridization vessel rotator and a liquid bath, the hybridization vessel rotator including means for holding a plurality of hybridization vessels and means for rotating said vessels, the means for holding hybridization vessels being supported by a frame which includes a base portion, the rotating means comprises a motor which is affixed to the frame at a position opposite to the base portion, the base portion being inserted into said bath such that the base portion and the vessels are substantially immersed in the bath, and such that the motor is outside said bath.

6. The combination of claim 5, wherein the motor is laterally offset relative to the base portion.

7. The combination of claim 5, wherein at least a portion of the motor is disposed directly above the base portion.

8. The combination of claim 5, wherein the motor is disposed in a housing, the combination further comprising blower means for creating a positive air flow across the motor and in the motor housing, thereby reducing condensation.

9. The combination of claim 5, wherein the frame includes an end plate which is removably attached to the base portion.

10. In combination, a hybridization vessel rotator and a temperature-controlled chamber, the hybridization vessel rotator including means for holding a plurality of hybridization vessels and means for rotating said vessels, the means for holding hybridization vessels being supported by a frame which includes a base portion, the rotating means comprises a motor which is affixed to the frame at a position opposite to the base portion, the hybridization vessel rotator being positioned entirely within said chamber, wherein the frame includes an end plate which is removably attached to the base portion.

11. The combination of claim 10, wherein the motor is laterally offset relative to the base portion.

12. The combination of claim 10, wherein at least a portion of the motor is disposed directly above the base portion.

13. The combination of claim 10, wherein the motor is disposed in a housing, the combination further comprising blower means for creating a positive air flow across the motor and in the housing, thereby reducing condensation.

14. A hybridization vessel rotator comprising:
a) a frame having a base portion and at least one upright portion for supporting a spindle, the spindle having means for removably affixing hybridization vessels to the spindle, and
b) a motor connected to turn the spindle,
wherein the motor is affixed to the upright portion of the frame at a position opposite the base portion,
wherein there are two upright portions, and wherein one of said upright portions is removably attached to the base portion.

15. The hybridization vessel rotator of claim 14, wherein the motor is laterally offset relative to the base portion.

16. The hybridization vessel rotator of claim 14, wherein at least a portion of the motor is disposed directly above the base portion.

17. The hybridization vessel rotator of claim 14, wherein the motor is mounted in a compartment which includes a fan, and wherein the fan comprises means for generating positive air pressure for reducing condensation in the motor compartment.

* * * * *